United States Patent [19]

Köhler et al.

[11] Patent Number: 5,387,718

[45] Date of Patent: Feb. 7, 1995

[54] METHOD OF MANUFACTURING ALKYLPHENYL ALKYL ETHERS OR ALKYLPHENYL ALKYL THIOETHERS

[75] Inventors: Günther Köhler, Marl; Peter Bickert, Münster, both of Germany

[73] Assignee: Huels Aktiengesellschaft, Marl, Germany

[21] Appl. No.: 913,192

[22] Filed: Jul. 14, 1992

[30] Foreign Application Priority Data

Aug. 13, 1991 [DE] Germany ............... 4126671

[51] Int. Cl.⁶ .............. C07C 319/14; C07C 41/01; C07C 41/16
[52] U.S. Cl. ..................... 568/38; 568/58; 568/426; 568/589; 568/630; 568/631; 568/632; 568/648; 568/650; 568/656; 568/658; 564/305; 564/440; 564/441; 564/442; 564/443; 560/17; 560/23; 560/43; 560/56; 560/61; 560/62; 560/63; 560/64; 560/65; 560/100; 560/103
[58] Field of Search ............ 568/658, 650, 38, 58, 568/631, 632, 426, 584, 656; 569/630, 648; 564/305, 440–443; 560/17, 23, 43, 56, 61–65, 100, 103

[56] References Cited

U.S. PATENT DOCUMENTS

| 4,192,949 | 3/1980 | Merger et al. | 560/67 |
| 4,310,706 | 1/1982 | Strege | 568/648 |
| 4,700,005 | 10/1987 | Green | 568/658 |

FOREIGN PATENT DOCUMENTS

| 162 | 1/1979 | European Pat. Off. | |
| 0104598 | 4/1984 | European Pat. Off. | 568/658 |
| 2595959 | 9/1987 | France | |
| 2026484 | 2/1980 | United Kingdom | |

OTHER PUBLICATIONS

Häfelinger, in "The Chemistry of Amidines and Imidates", 1975, John Wiley & Sons, Chapter 1, pp. 2–18, S. Patai, editor.

Schofield et al., in "The Azoles", 1976, Cambridge University Press, Table A.4., "Pyrazol-5-ones and Related Alkoxypyrazoles . . . 1,2,3-Triazoles".

*Primary Examiner*—Howard T. Mars
*Assistant Examiner*—Michael B. Hydorn
*Attorney, Agent, or Firm*—Oblon, Spivak, McClelland, Maier & Neustadt

[57] ABSTRACT

Alkylphenyl alkyl ethers or alkylphenyl alkyl thioethers, of the formula

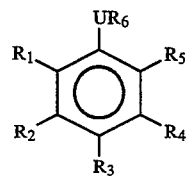

where U represents O or S; and $R_1$–$R_6$ each independently represent an alkyl or aryl group with 1–6 C atoms, but $R_1$–$R_5$ may each independently represent a functional group other than these, particularly —COOR (R=$C_{1-4}$ alkyl), —$NO_2$, —$NH_2$, —O—$CH_2$—$CH_2$—OH, —OH, —CHO, —H, or -halogen;

$R_1$–$R_5$ may be bridged by suitable bifunctional substituents, such as, e.g., —$(CH_2)_x$—, or —$(CH_2)_x$—Z—$(CH_2)_y$— (where Z represents a hetero atom; x=0–7 and y=0–7), or by unsaturated substituents or anellated ring systems; may be produced in high space-time yield by reacting the corresponding phenol or thiophenol with a arylalkyl carbonate at a temperature of 70°–300° C. under elevated or normal pressure, in the presence of a monocyclic, bicyclic, polycyclic, or acyclic amidine as a catalyst.

3 Claims, No Drawings

METHOD OF MANUFACTURING ALKYLPHENYL ALKYL ETHERS OR ALKYLPHENYL ALKYL THIOETHERS

BACKGROUND OF THE INVENTION

1. Field of the Invention

The present invention relates to a method of manufacturing alkylphenyl alkyl ethers or thioethers by reacting alkyl phenols or thiophenols with a dialkyl or arylalkyl carbonate, in the presence of amidine catalysts.

2. Discussion of the Background

Alkylphenyl alkyl ethers as considered herein comprise the oxygen ethers and the sulfur-derivative thioethers as well.

The phenyl ethers have the following formula:

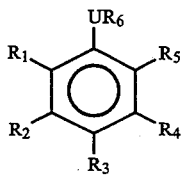

where U represents O or S; and $R_1-R_6$ each independently represent an alkyl or aryl group, but $R_1-R_5$ may each independently represent a functional group other than these, including, e.g., but not limited to, —COOR, —NO$_2$, —NH$_2$, —O—CH$_2$—CH$_2$—OH, —OH, —CHO, or -halogen; further $R_1-R_5$ may be bridged by suitable bifunctional substituents, such as, e.g., —(CH$_2$)$_x$—, or —(CH$_2$)$_x$—Z—(CH$_2$)$_y$— (where Z represents a hetero atom; x=0-7, and y=0-7), or preferably unsaturated substituents such as are characteristic of anellated ring systems, e.g. (but not limited to) naphthyl, phenanthryl, anthracenyl, quinolyl, isoquinolyl, or indolyl.

The alkylation of phenols and thiophenols is commonly carried out with alkyl esters of inorganic acids or with halocarboxylic acid esters, as disclosed in Houben-Weyl, "Methoden der organischen Chemie". The methods of manufacturing phenylalkyl ethers described in Eur. Pat. 0,000,162 are particularly advantageous, however. According to this publication, phenols are reacted with dimethyl carbonate in the presence of tertiary amines or tertiary phosphines. Eur. Pat. 0,104,598 also describes an alkylation method with dimethyl carbonate, wherewith sterically hindered alkylphenols can be alkylated in the presence of a tertiary amine such as 4-dimethylaminopyridine. Another methylation with dimethyl carbonate employing tertiary amines as catalysts is described in Eur. Pat. 0,315,334, wherewith the methylation substrate is a sugar derivative, dianhydrosorbitol.

In Fr. Pat. 2,595,959, the manufacture of alkylphenyl methyl ethers by reacting alkylphenols with dimethyl carbonate in the presence of substituted guanidines is described.

Lissel, M., et al., *Synthesis*, 382 (1986), reacted thiophenol with dimethyl carbonate in the presence of K$_2$CO$_3$ and crown ether, to obtain the corresponding thioether in about 80% yield.

The disadvantages of all of these methods are that the reactions are carried out with catalysts which:
- are toxic (e.g., phosphines and crown ether(s));
- are water pollutants (e.g., tertiary amines, quaternary ammonium salts, and guanidines);
- are expensive (e.g., crown ethers and guanidines);
- can be used only once (e.g., guanidines);
- afford low yields per unit volume per unit time (e.g., tertiary amines);
- in some cases can only promote the reaction under elevated pressure (e.g., phosphines).

A particular disadvantage of the ether formation catalyzed with guanidines is that these nitrogen bases tend to transfer substituents from the catalyst to the phenol which is undergoing alkylation—the result being the formation of undesirable by-products and a decrease in the effectiveness of the catalytically active guanidine system. This imposes major limitations, both as to the lifetime of the catalyst and in the choice of a suitable guanidine which will not lead to undesired side-reactions.

SUMMARY OF THE INVENTION

Accordingly, it is an object of the present invention to provide a method of manufacturing alkylphenyl alkyl ethers and alkylphenyl alkyl thioethers, wherein the catalysts employed are environmentally friendly, are readily available, and are reusable, and whereby the synthesis can be achieved at a high space-time yield and with minimal side reactions.

This object has been achieved by the inventors' discovery that the use of cyclic and acyclic amidine bases as catalysts yields alkylphenyl alkyl ethers or alkylphenyl alkyl thioethers in high space-time yields and that this method overcomes the above-described drawbacks.

DETAILED DESCRIPTION OF THE PREFERRED EMBODIMENTS

Thus, the present invention relates to a method of manufacturing alkylphenyl alkyl ethers or alkylphenyl alkyl thioethers of general formula

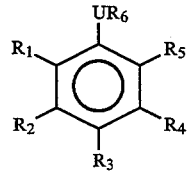

where U represents O or S; and $R_6$ represents a C$_{1-6}$ alkyl group or an aryl group with 6–12 C atoms; $R_1-R_5$ each independently represent a C$_{1-6}$ alkyl group or an aryl group with 6–12 C atoms or a functional group other than these, including, e.g., but not limited to, —COOR (R=C$_{1-4}$ alkyl), —NO$_2$, —NH$_2$, —O—CH$_2$—CH$_2$—OH, —OH, —CHO, —H, or -halogen; further $R_1-R_5$ may be bridged by suitable bifunctional substituents, such as, e.g., —(CH$_2$)$_x$—, or —(CH$_2$)$_x$—Z—(CH$_2$)$_y$— (where Z represents a hetero atom such as O, N, S; x=0-7 and y=0-7), or by unsaturated substituents (such as, straight-chain or branched C$_{2-6}$ alkenyl groups and straight-chain or branched C$_{2-6}$ alkynyl groups) or anellated ring systems; whereby the corresponding phenols or thiophenols are reacted with dialkyl carbonates or arylalkyl carbonates; characterized in that the process is carried out at a temperature of 70°–300° C. under elevated or normal pressure, in the presence of a monocyclic, bicyclic, polycyclic, or acyclic amidine as a catalyst.

Thus, in the context of the present invention, it is to be understood that the alkylphenyl alkyl ethers and alkylphenyl alkyl thioethers as well as corresponding starting material phenols and thiophenols include compounds in which adjacent pairs of $R_1$, $R_2$, $R_3$, $R_4$, and $R_5$ may together form a fused ring group, such as a benzo group, a naphtho group etc. In other words, the starting materials of the present process include, in addition to phenols and thiophenols, naphthols hydroxyphenanthrenes, hydroxyanthracenes, hydroxyquinolines, hydroxyisoquinolines, and hydroxyindoles, as well as the corresponding thiols. Thus, the products of the present process include the same polycyclic compounds.

The described ether formation is preferably carried out at pressures up to about 6 bar. Pressures >6 bar may also be used, but these are economically less advantageous.

Suitable amidines are all alkyl-, cycloalkyl-, and aryl-substituted amidines of formula I, as well as their hetero-substituted, bridged, and anellated bi- or polycyclic derivatives. Unsubstituted amidine ($R_1$=H, $R_2$=H, $R_3$=H, $R_4$=H) is unstable in the free state, and thus is not suitable.

Particularly suitable ether formation catalysts are amidines in which the amidine group is part of a ring system, e.g., in imidazolines, pyrimidines, 1,3-diazepines, and their anellated derivatives. Preferred examples of amidines are given below:

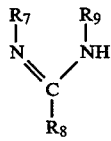
(I)

Where $R_7$–$R_9$ each independently represent H (provided that at least one of $R_7$, $R_8$, $R_9$, is not H), a straight-chain or branched $C_{1-12}$ alkyl group, a substituted or unsubstituted $C_{3-12}$ cycloalkyl, or a $C_{6-12}$ aryl group.

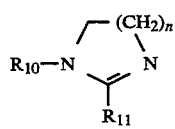
(II)

where n=1–6; and $R_{10}$ and $R_{11}$ are the same or different, each being a straight-chain or branched $C_{1-6}$ alkyl group, a $C_{3-6}$ cycloalkyl group, or a $C_{6-12}$ aryl group.

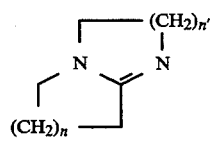
(III)

where n and n' each independently equal 1–6.

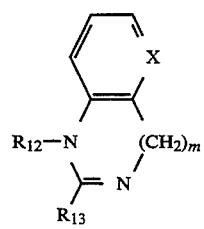
(IV)

where m=0–6;

$R_{12}$ and $R_{13}$ each independently represent a straight-chain or branched $C_{1-6}$ alkyl group, a $C_{3-6}$ cycloalkyl group, or a $C_{6-12}$ aryl group; and X represents O, N, or S.

The basicity of amidines is well known to be greater than that of tertiary amines but less than that of guanidines. Therefore it is surprising that amidines are better suited as ether formation catalysts than guanidines. An advantage of amidines over tertiary amines is that amidines have high resistance to oxidizing agents (Schwesinger, R., *Chimia*, vol. 39, p. 269 (1985); and Schwesinger and Missfeldt, *Angew. Chemie*, vol. 99, p. 1210 (1987)). Consequently, amidine catalysts exhibit superior storage stability to that of tertiary amine catalysts.

The reaction of phenols with dimethyl carbonate can be represented by the following formula:

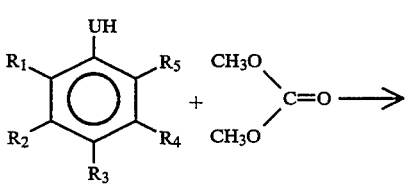

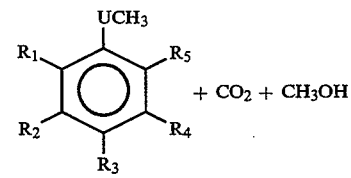

where U represents O or S.

In comparison to the known methods, according to the present invention alkylphenyl alkyl ethers are obtained in good yields and high purity. The only by-products are $CO_2$ and alcohol, which may be regarded as un-problematic as regards environmental protection.

It was surprising in the light of known methods that the reaction, for most phenols, led to nearly complete conversion ($\geq 98\%$) in less than 5 hr at normal pressure, and in less than 3 hr at slightly elevated pressure. It is particularly advantageous that the catalyst can be reused numerous times, being retained unchanged in the bottoms after the distillation following the conclusion of the reaction. After fresh phenol is added, along with the appropriate dose of dimethyl carbonate, the inventively employed catalyst can be reused at least 10 times, with almost the same phenol conversion as the first time. The method is adaptable to continuous operation.

The phenol is nearly completely converted in 2–4 hr, under normal pressure or slightly elevated pressure. The same high space-time yields can be attained with or without inert solvents.

Examples of candidates for use as starting phenols are: phenol, pyrocatechol, hydroquinone, resorcinol, 1,3,5-trihydroxybenzene, 1,2,3-trihydroxybenzene, o-, m-, and p-cresol, 2,3-, 2,4-, 2,5-, 2,6-, 3,5-, and 3,4-dihydroxyxylene, 3,4-isopropylphenol, 2,3,4-n-butylphenol, 2-, 3-, or 4-sec-butylphenol, 2-, 3-, or 4-isobutylphenol, 2,4,6-trimethylphenol, 2-isopropyl-5-methylphenol, 2- or 4-tert-butylphenol, 2,5-di-tert-butylphenol, 2,5-dimethyl-4-tert-butylphenol, 2- or 4-cyclohexylphenol, 4-n-hexylphenol, 4-n-octylphenol, salicylic acid or its esters, salicylaldehyde, eugenol, iso-eugenol, vanillin, α- or β-naphthol, 2- or 4-aminophenol, anisaldehyde, anisic acid or its esters, pyrocatechol monomethyl ether, and 4-tert-butylpyrocatechol. Analogously, the corresponding thiophenols are also candidates.

Preferred dialkyl or arylalkyl carbonates are: dimethyl carbonate, diethyl carbonate, methyl ethyl carbonate, di-n-propyl carbonate, di-n-butyl carbonate, and dibenzyl carbonate.

The amidines used as catalysts are charged in an amount of 0.1–10 wt. %, preferably 0.5 to 5 wt. %, (based on the weight of the phenol used). Particularly suitable amidines are: 1,3-diazepines, diazabicyclo[2.4.6-]dodecatriene, 1,5- diazabicyclo-3-octene, diazabicycloundecene, 4,5-dihydro-2-phenylimidazole, 4,5-dihydro-2-methylimidazole (Lysidin), N,N'-dibenzylbenzamidine, and N,N'-dicyclohexylbenzamidine.

It is also possible to proceed in the presence of solvents. Suitable solvents are inert and high-boiling, e.g. xylene, mesitylene, nonane, decane, and N-methylpyrrolidone. The temperature for the reaction is suitably 70°–300° C., preferably 130°–190° C. Normal pressure is used, or slightly elevated pressure (up to 6 bar). According to the present invention, the method can also be carried out at >6 bar. The process may be continuous or discontinuous. The ratio of phenol or thiophenol to dialkyl carbonate or diaryl carbonate is suitably from 0.5:1.0 to 1:0.5. Preferably, a slight excess of dialkyl carbonate or arylalkyl carbonate is used, and the preferred ratio of phenol or thiophenol to dialkyl carbonate or diaryl carbonate is from about 1:1 to about 1:1.2.

The products synthesized according to the method are important intermediate products, or may themselves be used as fragrances, drugs, plant protection agents, or stabilizers for oils used in food and feed.

Other features of the invention will become apparent in the course of the following descriptions of exemplary embodiments which are given for illustration of the invention and are not intended to be limiting thereof.

EXAMPLES

Example 1

10 mol of p-tert-butylphenol, along with 0.2 mol of 1,5-diazabicyclo[4.3.0]-5-nonene (DBN), were charged into a reactor with a stirrer, and together with a solvent such as decane were heated to 160° C. Then, 12 mol of dimethyl carbonate was added at a uniform or regularized rate over a period of 4 hr, through an inlet tube extending to the bottom of the reactor. The methanol produced in the reaction (along with the $CO_2$) was removed by distillation over a column. This ensured that the reaction temperature would not fall.

After completion of the reaction, 9.5 mol of p-tert-butylphenyl methyl ether was obtained, which (after distillation) represented a 95% yield, based on the starting amount of p-tert-butylphenol. In the bottoms, 0.18 mol of the diazabicyclononene remained, unchanged.

Example 2

15 mol of eugenol was charged into a pressure reactor, along with 0.2 mol of 1,8-diazabicyclo[5.4.0]-7-undecene and 16 mol of dimethyl carbonate. The reactor was sealed and was heated to 150° C. After 2 hr, complete conversion of the eugenol was shown to have occurred. After the distillation, 13 mol of eugenol methyl ether and 1 mol of isoeugenol methyl ether were obtained, corresponding to a yield of 86%, based on the starting amount of eugenol.

Example 4

5 mol of β-naphthol was charged into a tubular autoclave, along with 6 mol of dimethyl carbonate and 0.25 mol of 4,5-dihydro-2-phenylimidazole, and the mixture was heated to 140° C. After 2.5 hr, complete conversion of the βd-naphthol was determined by gas chromatography.

After distillative refinement, 4.5 mol of β-naphthyl methyl ether was obtained.

Example 5

10 mol of 2-nitrophenol was charged into a stirred, heated reactor, along with 800 ml of nonane and 5% N,N'-dimethylbenzoamidine, and the mixture was heated to 150° C. Then 12 mol of dimethyl carbonate was added portionwise over 5 hr. The methanol produced by the reaction was removed by distillation over a distillation column. After completion of the reaction, the reaction mixture was refined by distillation. 2-Nitroanisole was obtained in the amount of about 9 mol, corresponding to a yield of c. 90%, based on the starting amount of 2-nitrophenol.

Example 6

5 mol of o-tert-butylphenol was charged into a reactor, along with 400 ml of decane and 5% of 4,5-dihydro-2-phenylimidazole, and the mixture was heated to 140° C. Then 5.5 mol of diethyl carbonate was added portionwise over a period of 4 hr. The resulting ethanol was continuously removed by distillation from the reaction mixture. After completion of the reaction, 4.6 mol of o-tert-butylphenyl ethyl ether was obtained from the mixture by distillation. The yield corresponded to 92% of theoretical, based on the starting amount of o-tert-butylphenol.

Example 7

1 mol of thiophenol was charged into a reactor, along with 100 ml of nonane and 5% of 1,5-diazabicyclo[4.3.0]-5-nonene, and the mixture was heated to 150° C. Then 1.2 mol of dimethyl carbonate was added portionwise over a period of 4 hr. The methanol produced was removed by distillation from the reaction mixture. After completion of the reaction, and refinement by distillation, thioanisole was obtained with a yield of 88%, based on the starting amount of thiophenol.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method of preparing an alkylphenyl alkyl ether or an alkylphenyl alkyl thioether, of the formula

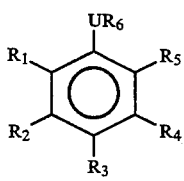

where U represents O or S; and $R_6$ is a $C_{1-6}$ alkyl group or an aryl group with 6–12 C atoms; $R_1$–$R_5$ are independently a $C_{1-6}$ alkyl group, an aryl group with 6–12 C atoms, H, —COOR where R is a $C_{1-4}$ alkyl, —NO$_2$, —NH$_2$, —O—CH$_2$—CH$_2$—OH, —OH, —CHO, or halogen; any two of $R_1$–$R_5$ can be bridged by a bifunctional substituent of the formula —(CH$_2$)$_x$— or —(CH$_2$)$_x$—Z—(CH$_2$)$_y$, where Z represents a hetero atom; x is an integer of from 0 to 7 and y is an integer from 0 to 7, by an unsaturated substituent selected from the group consisting of a straight-chain $C_{2-6}$ alkenyl group, a branched $C_{2-6}$ alkenyl group, a straight-chain $C_{2-6}$ alkynyl group and a branched $C_{2-6}$ alkynyl group, or by an anellated ring system; comprising contacting a phenol or thiophenol having the formula

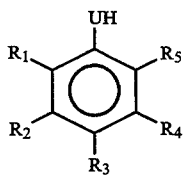

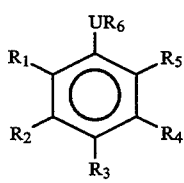

in which $R_1$–$R_5$ are as defined above, with a dialkyl carbonate or arylalkyl carbonate having the formula

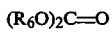

(R$_6$O)$_2$C=O wherein $R_6$ is as defined above; wherein said phenol or thiophenol is capable of reacting with said dialkyl carbonate or arylalkyl carbonate, said contacting is carried out at a temperature of 70°–300° C. under elevated or normal pressure, in the presence of 0.1–10 wt. %, based on the weight of phenol or thiophenol used, of an amidine catalyst, wherein said amidine catalyst is a cyclic amidine of the formula

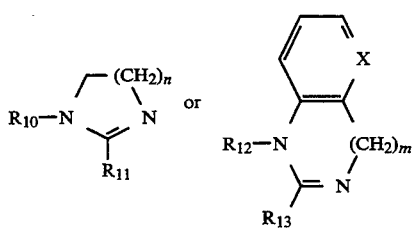

wherein n is an integer from 1 to 6, m is an integer from 1 to 6, $R_{10}$ is H, $C_1$–$C_6$ alkyl, $C_{6-12}$ aryl or $C_{3-6}$ cycloalkyl, $R_{11}$ is $C_{6-12}$ aryl or $C_{3-6}$ cycloalkyl, $R_{12}$ and $R_{13}$ are each, independently, $C_1$–$C_6$ alkyl, $C_{6-12}$ aryl or $C_{3-6}$ cycloalkyl, and X is N, or S.

2. A method of preparing an alkylphenyl alkyl ether or an alkylphenyl alkyl thioether, of the formula

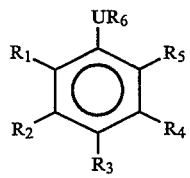

where U represents O or S; and $R_6$ is a $C_{1-6}$ alkyl group or an aryl group with 6–12 C atoms; $R_1$–$R_5$ are independently a $C_{1-6}$ alkyl group, an aryl group with 6–12 C atoms, H, —COOR where R is a $C_{1-4}$ alkyl, —NO$_2$, —NH$_2$, —O—CH$_2$—CH$_2$—OH, —OH, —CHO, or halogen; any two of $R_1$–$R_5$ can be bridged by a bifunctional substituent of the formula —(CH$_2$)$_x$— or —(CH$_2$)$_x$—Z—(CH$_2$)$_y$, where Z represents a hetero atom; x is an integer of from 0 to 7 and y is an integer from 0 to 7, by an unsaturated substituent selected from the group consisting of a straight-chain $C_{2-6}$ alkenyl group, a branched $C_{2-6}$ alkenyl group, a straight-chain $C_{2-6}$ alkynyl group and a branched $C_{2-6}$ alkynyl group, or by an anellated ring system; comprising contacting a phenol or thiophenol having the formula

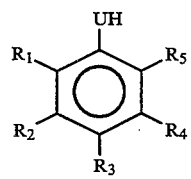

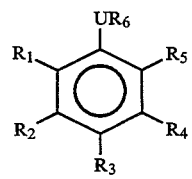

in which $R_1$–$R_5$ are as defined above with a dialkyl carbonate or arylalkyl carbonate having the formula

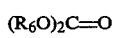

(R$_6$O)$_2$C=O wherein $R_6$ is as defined above; wherein said phenol or thiophenol is capable of reacting with said dialkyl carbonate or arylalkyl carbonate, said contacting is carried out at a temperature of 70°–300° C. under elevated or normal pressure, in the presence of 0.1–10 wt. %, based on the weight of phenol or thiophenol used, of an amidine catalyst, wherein said amidine catalyst is a cyclic amidine of the formula

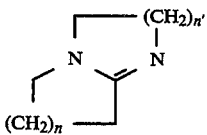

wherein n and n' are each independently an integer from 1 to 6.

3. A method of preparing an alkylphenyl alkyl ether or an alkylphenyl alkyl thioether, of the formula

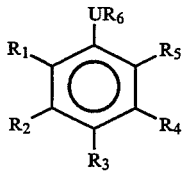

where U represents O or S; and $R_6$ is a $C_{1-6}$ alkyl group or an aryl group with 6–12 C atoms; $R_1$–$R_5$ are independently a $C_{1-6}$ alkyl group, an aryl group with 6–12 C atoms, H, —COOR where R is a $C_{1-4}$ alkyl, —NO$_2$, —NH$_2$, —O—CH$_2$—CH$_2$—OH, —OH, —CHO, or halogen; any two of $R_1$–$R_5$ can be bridged by a bifunctional substituent of the formula —(CH$_2$)$_x$— or —(CH$_2$)$_x$—Z—(CH$_2$)$_y$, where Z represents a hetero atom; x is an integer of from 0 to 7 and y is an integer from 0 to 7, by an unsaturated substituent selected from the group consisting of a straight-chain $C_{2-6}$ alkenyl group, a branched $C_{2-6}$ alkenyl group, a straight-chain $C_{2-6}$ alkynyl group and a branched $C_{2-6}$ alkynyl group, or by an anellated ring system; comprising contacting a phenol or thiophenol having the formula

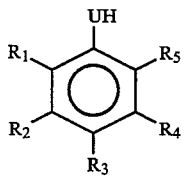

with a dialkyl carbonate or arylalkyl carbonate having the formula

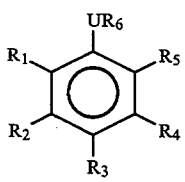

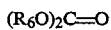

wherein $R_6$ is as defined above; wherein said phenol or thiophenol is capable of reacting with said dialkyl carbonate or arylalkyl carbonate, said contacting is carried out at a temperature of 70°–300° C. under elevated or normal pressure, in the presence of 0.1–10 wt. %, based on the weight of phenol or thiophenol used, of 4,5-dihydro-2-phenylimidazole.

* * * * *